(12) United States Patent
Serebrennikov

(10) Patent No.: US 6,413,713 B1
(45) Date of Patent: Jul. 2, 2002

(54) METHOD FOR PRESERVING BLOOD PLATELETS

(75) Inventor: Vladimir L. Serebrennikov, Krasonyarosk (RU)

(73) Assignee: HyperBaric Systems, Palo Alto, CA (US)

( * ) Notice: Subject to any disclaimer, the term of this patent is extended or adjusted under 35 U.S.C. 154(b) by 0 days.

(21) Appl. No.: 09/183,581

(22) Filed: Oct. 30, 1998

(51) Int. Cl.⁷ .................. A01N 1/02; A61K 47/42
(52) U.S. Cl. ........................... 435/2; 514/774
(58) Field of Search ................ 435/2; 514/774

(56) References Cited

U.S. PATENT DOCUMENTS

| | | | | |
|---|---|---|---|---|
| 2,662,520 A | | 12/1953 | McMahon | 128/1 |
| 2,786,014 A | | 3/1957 | Tullis | 167/78 |
| 3,729,947 A | * | 5/1973 | Higuchi | |
| 3,753,357 A | | 8/1973 | Schwartz | 62/64 |
| 3,841,515 A | | 10/1974 | Schwartz | 220/3 |
| 4,059,967 A | * | 11/1977 | Rowe et al. | |
| 4,639,373 A | * | 1/1987 | Babior | |
| 4,764,463 A | * | 8/1988 | Mason et al. | |
| RE32,874 E | * | 2/1989 | Rock et al. | |
| 5,487,971 A | * | 1/1996 | Holme et al. | |
| 5,554,527 A | * | 9/1996 | Fickenscher | |
| 5,635,344 A | | 6/1997 | Garcia et al. | 435/1.1 |

FOREIGN PATENT DOCUMENTS

| | | |
|---|---|---|
| EP | 0 232 672 | 8/1987 |
| FR | 2 600 671 | 12/1987 |
| SU | 1124974 | 11/1984 |

* cited by examiner

Primary Examiner—Jon P. Weber
(74) Attorney, Agent, or Firm—Wilson Sonsini Goodrich & Rosati

(57) ABSTRACT

A method for preserving blood platelets is described. The method uses 1%–3% gelatin in the platelet preservation medium, and storing the platelets in the preservation medium at temperatures below 0° C. and at least 70 atmospheres pressure for at least one day.

11 Claims, 7 Drawing Sheets

METHOD FOR PRESERVING BLOOD PLATELETS

BACKGROUND OF THE INVENTION

1. Field of the Invention

The present invention relates to method and apparatus for preserving biological materials. More particularly, the invention relates to method and apparatus for preserving biological materials which employs a combination of a preservation solution, high pressure, and low temperature.

2. Description of Related Art

Whole blood and blood components including leukocytes, erythrocytes, thrombocytes, and plasma, need to be preserved and stored until needed for use. Skin and other tissue, kidneys, hearts, livers, and other organs need to preserved and stored until needed for use. These and other biological materials are preserved and stored using both freezing and non-freezing temperatures.

Freezing temperatures require the use of cryoprotectors such as DMSO (dimethyl sulfoxide) and Thrombosol™ to prevent damage to these biological materials. However, these cryoprotectors are cytotoxic, and typically leave a significant portion of the materials with either reduced or no functional ability. Moreover, cryoprotectors usually require time-consuming preparation, such as rinsing processes, before the materials can be used, and cryoprotector residues often still remain afterwards. Freezing processes can store erythrocytes for more than 30 days, and leukocytes up to 12 hours only.

Non-freezing temperatures limit the amount of time biological materials may be stored and preserved. In addition, non-freezing temperatures may require additional protocols. For example, platelets require mechanical agitation to prevent clumping, and can be stored this way for up to 5 days only.

What is needed are a method and apparatus for preserving biological materials for greater periods of time than with currently available methods and apparatus.

SUMMARY OF THE INVENTION

The present invention describes a method for preserving biological materials. The method includes applying a preservation solution to a biological material, and then storing the biological material at a pressure greater than 70 atm and a temperature less than 10° C.

The present invention also describes an apparatus for preserving biological materials. The apparatus includes a chamber having a mouth and a lip, the lip having an inside surface and a top surface, the inside surface and the top surface of the lip meeting at a first radius, the top surface of the lip having a channel. The apparatus also includes a cover configured to mate with and seal the chamber, the cover having a bottom surface, the bottom surface having a protrusion and a sealing structure, the bottom surface of the cover and the protrusion meeting at a second radius, the protrusion being inserted into the mouth of the chamber when the cover is mated with the chamber, the protrusion having a side surface, the side surface of the protrusion and the inside surface of the lip defining a first gap and being substantially parallel when the cover is mated with the chamber, the bottom surface of the cover and the top surface of the lip defining a second gap and being substantially parallel when the cover is mated with the chamber, the second gap having a length greater than a width of the first gap, the sealing structure being inserted into the channel of the lip when the cover is mated with the chamber.

DETAILED DESCRIPTION OF THE INVENTION

Figure 1:
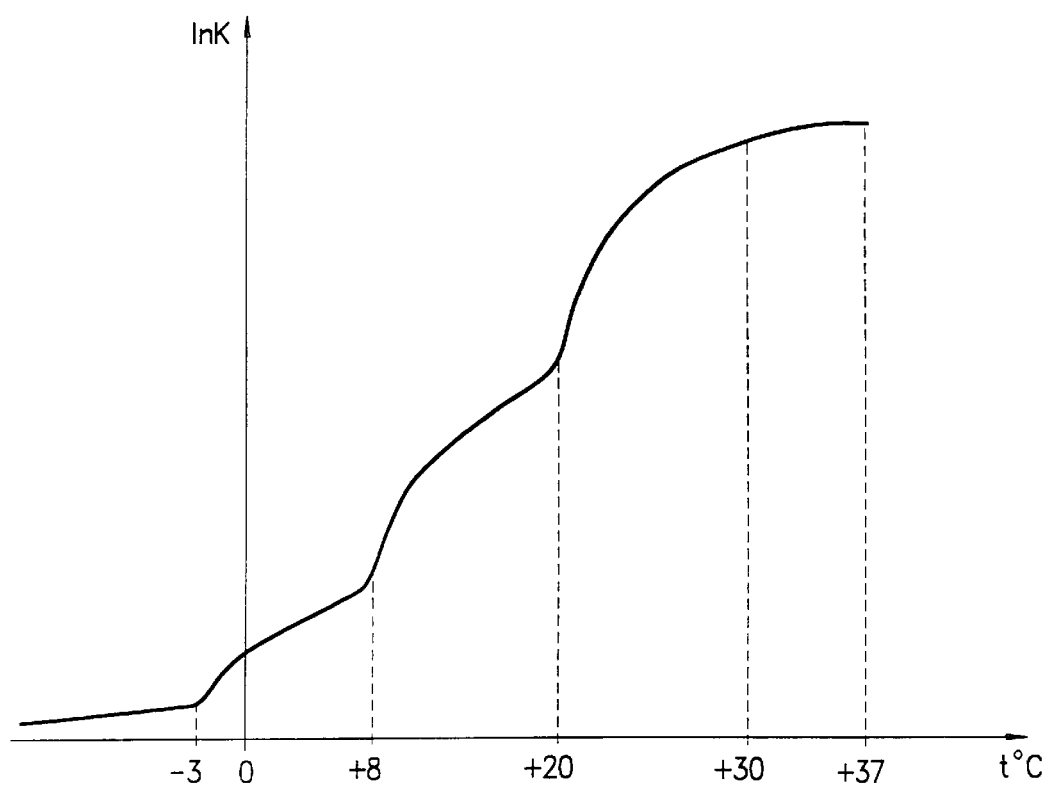
FIG. 1 shows a graph of ln K versus temperature for rate of biochemical reaction.

The method of the present invention is capable of preserving blood, tissue, organs, and other biological materials for greater periods of time than with currently available methods. This is achieved by using a combination of: (1) a preservation solution having a gel state at the low storage temperatures employed; (2) high storage pressures greater than 70 atm; and (3) low storage temperatures less than 10° C.

I. Introduction

Temperature is one of the most important parameters to be considered when storing living biological materials. When the temperature inside a cell drops too low, irreversible biochemical and structural changes occur. Several hundred biochemical reactions take place concurrently in the living cell. The rate of these biochemical reactions depends on several factors, including pressure, temperature, viscosity of the environment, pH, and concentrations of reactive molecules.

A metabolic process typically includes a series of intermediate processes, in which a substrate S is converted into a series of intermediate products $X_1, X_2, X_3 \ldots$ before being converted into a final product P. For each of these intermediate processes, the reactions may be catalyzed with different enzymes $E_o, E_1, E_2 \ldots$:

$$S \xrightarrow{E_o} X_1 \xrightarrow{E_1} X_2 \xrightarrow{E_2} X_3 \ldots \rightarrow P \qquad \text{Equation (1)}$$

Under normal conditions, the volume of substrate S transformed per unit of time equals the volume of product P obtained per unit of time:

$$-\frac{d[S]}{dt} = +\frac{d[P]}{dt} \qquad \text{Equation (2)}$$

where [S] and [P] are the concentrations of substrate S and product P. The concentration of the intermediate products $[X_1], [X_2], [X_3]$ under such conditions should also be constant:

$$\frac{d[X_1]}{dt} = \frac{d[X_2]}{dt} = \frac{d[X_3]}{dt} = 0 \qquad \text{Equation (3)}$$

Therefore, for each intermediate product, its rate of formation equals its rate of transformation. The concentrations of each intermediate product may be expressed in terms of the rates of formation and transformation:

$$\frac{d[X_3]}{dt} = -\frac{d[X_2]}{dt} = K_2 \cdot [X_2] \qquad \text{Equation (4)}$$

where $K_2$ is the constant of rate reaction constant of transformation of product $X_2$ and formation of product $X_3$. For steady state:

$$-\frac{d[S]}{dt} = +\frac{d[X_1]}{dt} = +\frac{d[X_2]}{dt} = +\frac{d[X_3]}{dt} \ldots = +\frac{d[P]}{dt} \qquad \text{Equation (5)}$$

From the above it follows that:

$$K_1 \cdot [X_1] = K_2 \cdot [X_2]$$

$$[X_1]:[X_2] = K_2:K_1 \qquad \text{Equation (6)}$$

Therefore, the concentration of each intermediate product is determined by its rate constants of formation and transformation.

Temperature dependence is defined by constant K of the rate of chemical reaction to Arrenius:

$$K = A \cdot e^{-E/RT} \qquad \text{Equation (7)}$$

where

A is the constant coefficient in some temperature interval;

E is the activating energy of chemical reaction per 1 mol of the substance;

R is the universal gas constant; and

T is the absolute temperature.

For most biochemical reactions, $E \gg RT$. Taking the natural logarithm of both sides of Equation (7) gives:

$$\ln K = \ln A - \frac{E}{RT} \qquad \text{Equation (8)}$$

FIG. 1 shows a graph of ln K versus temperature. From 30° C. to 37° C., A is constant. For different chemical reactions E and A are different. As temperature decreases, there is a misbalance of reactions rates and Equation (5) no longer holds. This means the intermediate product concentrations corresponding to each of the biochemical reactions begin to change. This begins breakdown of cell structures, including the cell membrane, and can end in cell death.

Chemical reactions are either exothermic or endothermic, i.e. they either give off or absorb energy. Reactions taking place during hydrolysis can release large amounts of energy. The oxidation of 1 mol of glucose releases 2883 kJ of energy. Should the biochemical reaction rates slow down too much, irreversible process begin to take place finally leading to total destruction of the cell. Therefore, coefficient A becomes a function of temperature T.

As the temperature drops below 20° C., the lipid bi-lay of the cell membrane undergoes a phase transmission from a colloid to a gel. The viscosity of a gel is much higher then that of its colloid. Consequently, rates of diffusion and active transportation of molecules through the cell membrane decrease sharply, resulting in a slowing down of the rate of biochemical reactions in a cell. As a result of the phase transformation of the cell membrane, the surface area of the lipid bi-lay surface and cell size reduce considerably due to the loss of water from the cell.

As the density of osmo-active substances increases, water molecules return to the cell thereby increasing osmotic pressure. Membrane tension reaches a critical point and may lose its barrier function. Membrane damage develops, resulting in morphological and structural changes, as well as loss of the ability for active adaptation.

As the temperature drops below 8° C., the cell cytoplasma undergoes a phase transformation into a gel. At this temperature, there is a sharp decrease in diffusion rate and active transportation of molecules, as well as in biochemical reaction rates.

As the temperature falls below −3° C., water crystallization begins to occur both inside and outside the cell. In the absence of cryoprotectors, water crystallization outside the cell leads to cell dehydration, decreased cell size, and increased concentrations of salt and other substances inside the cell. Water crystallization inside the cell results in structural cell membrane destruction.

In light of the above, the method and apparatus of the present invention seek to achieve the following:

1. Using a preservation solution which forms a viscous gel to mechanically suspend the biological materials.
2. Storing the biological materials at the lowest possible temperature while maintaining them in a liquid state. Under these conditions, the rate of biochemical reactions are relatively slow and therefore, the rates of change in the concentrations of intermediate products is small.
3. Slowly cooling solutions with platelets to allow free and safe water flow from the cell to prevent membrane tension from reaching a bursting point during the phase transmission from a colloid to a gel. On the other hand, the cooling rate should be high enough to prevent intermediate biochemical reactions from causing irreversible changes in cell structure.

II. Method

One embodiment of a method for preserving a biological material comprises: (1) applying a preservation solution to the biological material; (2) storing the biological material at a low temperature and a high pressure.

The preservation solution includes 1 to 3% gelatin. As it is cooled, the gelatin undergoes a phase transformation between 8° C. and 15° C. from a colloid to a gel. This gel suspends cells in the preservation solution. The gel reduces sedimentation and clumping of platelets. The gel also mechanically supports the cell membrane and reduces deformation of the membrane when the interior volume of the cell changes during the cooling process. The gel also lowers cell metabolism by decreasing exchange between the cell and its environment.

The preservation solution may also include sucrose, glucose, and/or sodium chloride. The sucrose repairs damage in the cell membrane caused by the cooling process. The glucose provides nutrients to sustain cell metabolism in the oxygen-poor conditions caused by the cooling process. Glycolysis produces 208 J/mol. The sucrose and glucose also bind water, thus promoting gel formation and inhibiting osmotic pressure build-up within the cell.

The sodium chloride prevents hemolysis by inhibiting the flow of water to the platelets during cooling. As the platelets are cooled below 20° C., the cytoplasma changes from a colloid to a gel, and free water leaves the cell. As the platelets are cooled even further, the hypertonic concentration of NaCl prevents water from reentering the platelets. The sodium chloride also lowers the freezing point of blood plasma by 2.5° C.

In one embodiment, the preservation solution includes 1.0 to 3.0% gelatin, 1.0 to 2.0% glucose, 1.0 to 3.0% sucrose, and 0.2 to 0.6% NaCl. In another embodiment, the preservation solution includes 2.9% gelatin, 0.44% sucrose, 1.17% glucose, and 0.49% NaCl.

The biological material is stored at a pressure greater than 70 atm and a temperature less than 10° C. In one embodiment, the biological material is stored at a pressure in the range of 70 to 1000 atm and a temperature in the range of −12° C. to 0° C. In another embodiment, the biological material is stored at a pressure in the range of 400 to 500 atm and a temperature in the range of −8° C. to −7° C.

Figure 2:
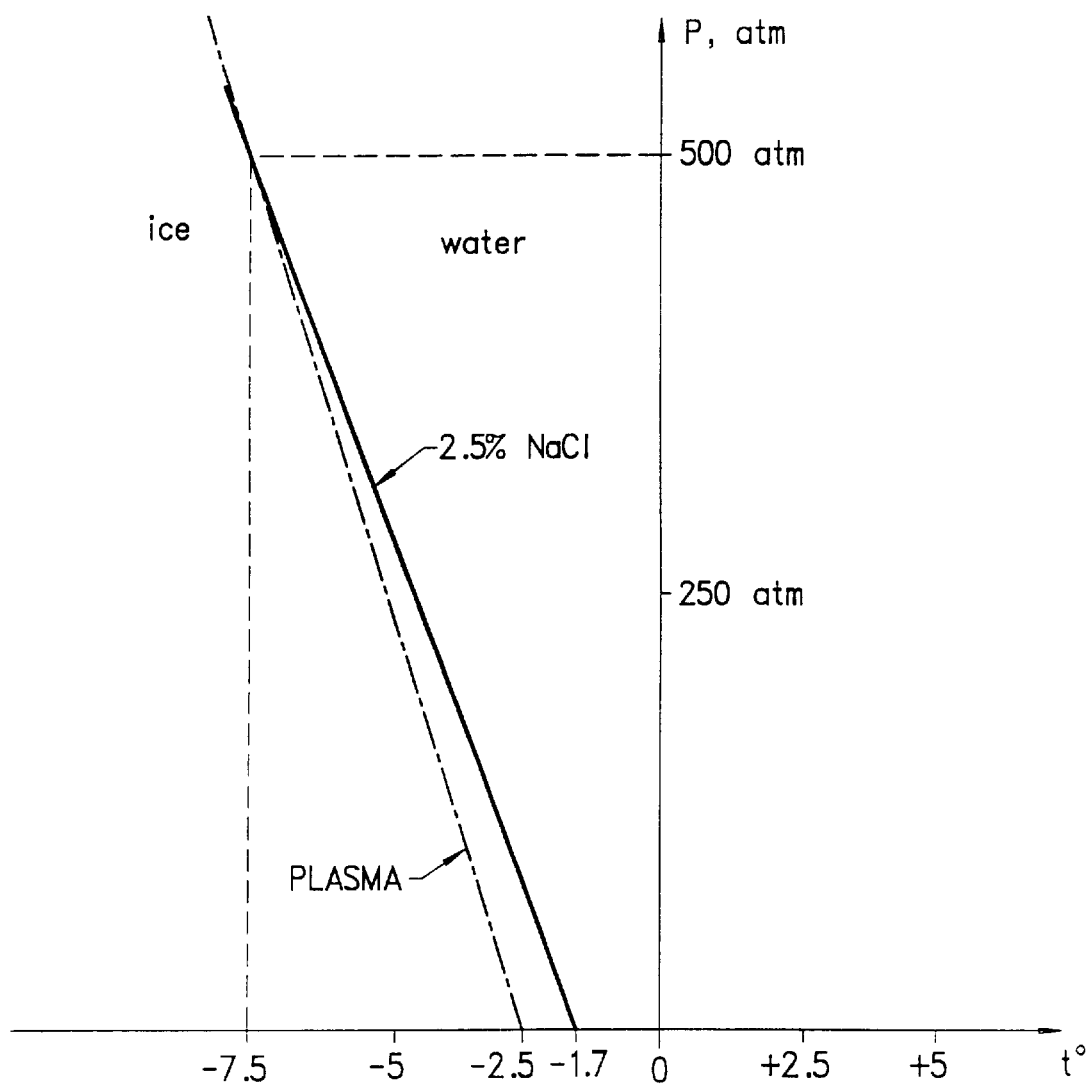
FIG. 2 the phase transition lines for plasma and a 2.5% NaCl solution.

FIG. 2 shows the phase transition lines for plasma and a 2.5% NaCl solution. At normal pressures, plasma freezes at −2.5° C. Plasma contains various chemical which lower the freezing point by interfering with the formation of the crystal lattice structure of ice. Cell structures can be cooled to −4° C. to −3° C. without water crystallization into cytoplasma. At normal pressures, the 2.5% NaCl solution freezes at −1.7° C.

Figure 3:
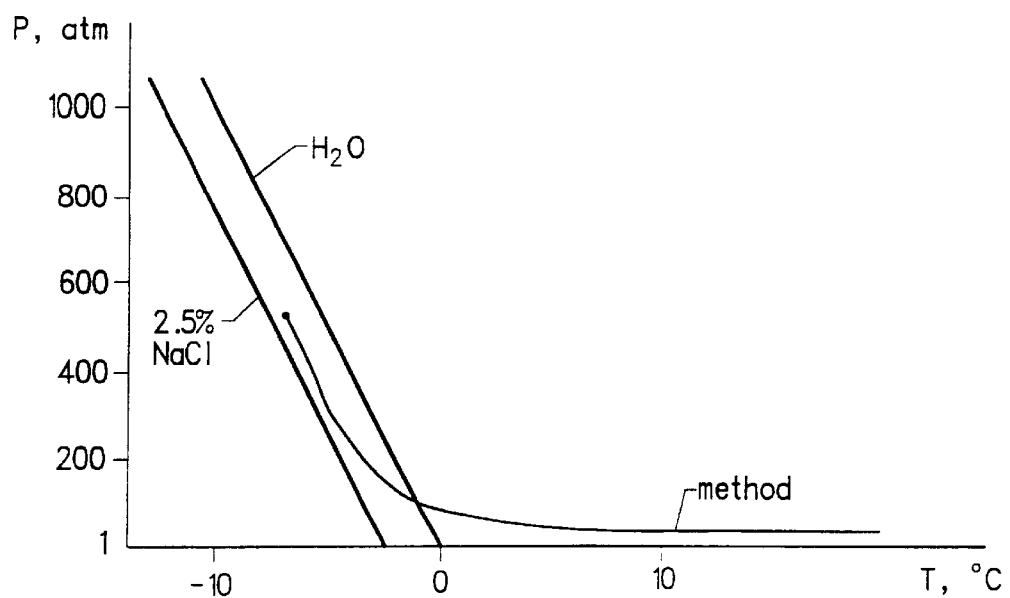
FIG. 3 shows another set of phase transition lines.

FIG. 3 shows the phase transition lines for water and a 2.5% NaCl solution. The addition of NaCl to water as lowers the freezing point, and thus allows lower temperatures to be achieved for a given pressure. The method line shows one example of how a biological material may be subjected to a combination of high pressure and low temperature to prevent freezing.

III. Apparatus

Figures 4, 4A:
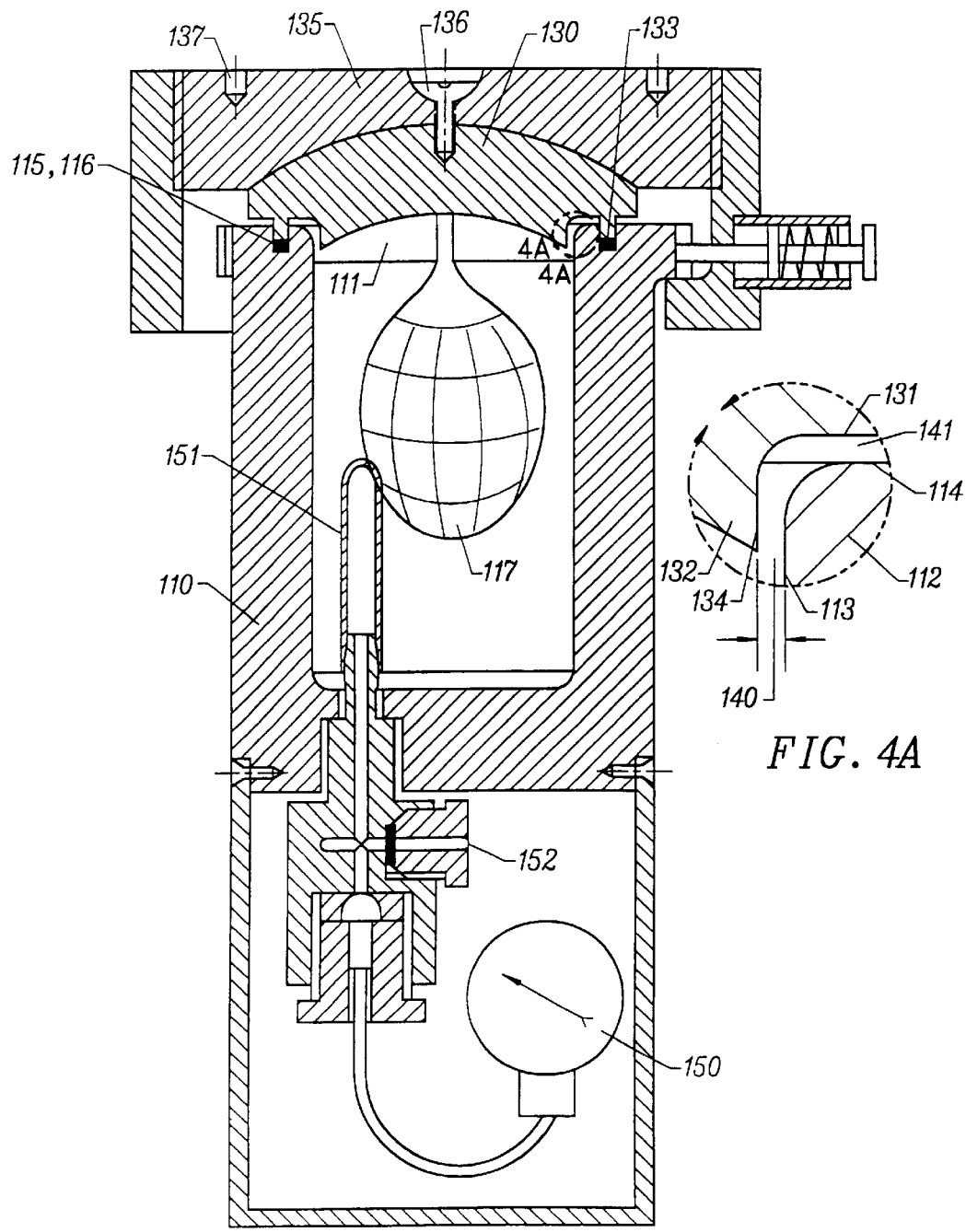
FIG. 4 shows a cross-sectional view of a biological material preservation apparatus of the present invention.

FIG. 4 shows an assembled view of one embodiment of a biological material preservation apparatus 100 of the present invention. Preservation apparatus 100 includes a chamber 110 and a cover 130.

Figure 5A:
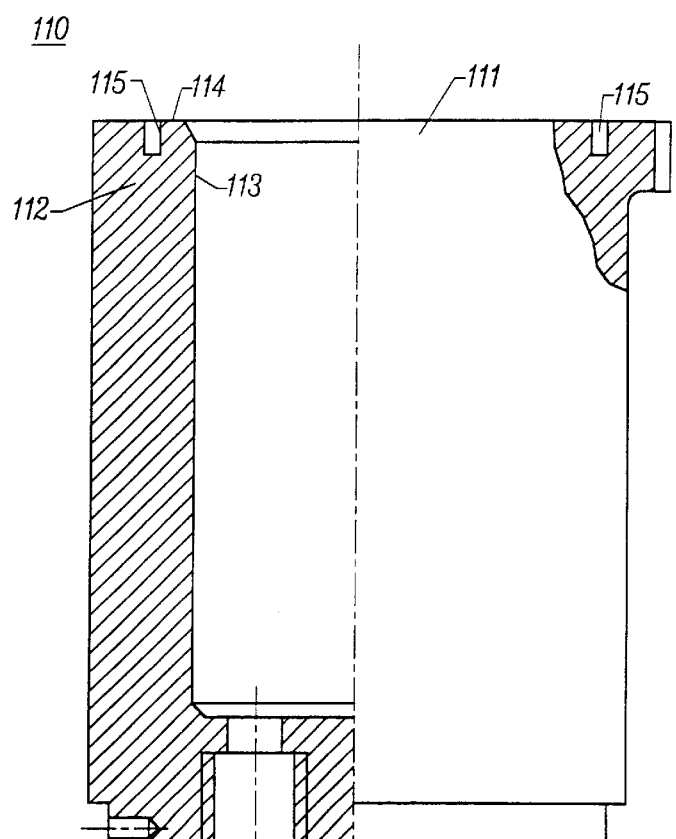
FIGS. 5A–5B shows a side cutaway and top views, respectively, of the chamber of the preservation apparatus.
Figure 5B:
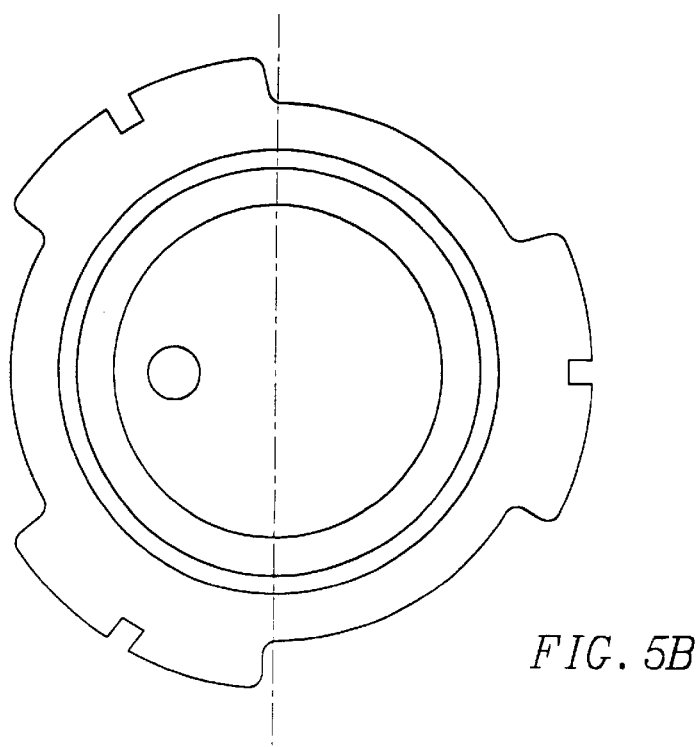

FIGS. 5A–5B show side cutaway and top views, respectively, of chamber 110. Chamber 110 includes a mouth 111 and a lip 112. Lip 112 includes an inside surface 113 and a top surface 114. Inside surface 113 and top surface 114 meet at a first radius $r_1$. Top surface 114 includes a channel 115. Channel 115 may have a sealing device 116 seated at a bottom of channel 115, such as an O-ring or rubber gasket. Chamber 110 may be manufactured in different sizes to accommodate a platelet bag, blood donation bag, heart, liver, kidney, or other bags and biological materials.

Figure 6:
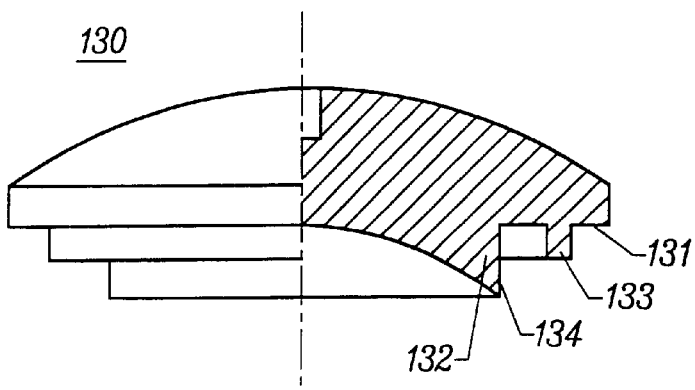
FIG. 6 shows a side view of the cover of the preservation apparatus.

FIG. 6 shows a cutaway view of cover 130. Cover 130 is configured to mate with and seal chamber 110. Cover 130 includes a bottom surface 131. Bottom surface 131 includes a protrusion 132 and a sealing structure 133. Bottom surface 131 and protrusion 132 meet at a second radius $r_2$. Protrusion 132 is inserted into mouth 111 of chamber 110 when cover 130 is mated with chamber 110. Protrusion 132 includes a side surface 134. Side surface 134 of protrusion 132 and inside surface 113 of lip 112 define a first gap 140 and are substantially parallel when cover 130 is mated with chamber 110. Bottom surface 132 of cover 130 and top surface 118 of lip 114 define a second gap 141 and are substantially parallel when cover 130 is mated with chamber 110. Second gap 141 has a length greater than a width of first gap 140. Sealing structure 133 is inserted into channel 115 of lip 112 when cover 130 is mated with chamber 110.

Cover 130 may be made to be a spherical section, which allows cover 130 to be made lighter and with less material than a flat cover 130 without sacrificing strength. When preservation apparatus 100 is filled with, for example, saline solution and then cooled below the freezing point, ice will begin to form along the walls of chamber 110 and cover 130. Ice will form in first gap 140 and second gap 141 and help to seal chamber 110. Thus, the high pressures within chamber 110 are largely borne by this ice seal, thus minimizing the need to make channel 115, sealing device 116, and sealing structure 133 extremely robust and capable of withstanding such high pressures. Channel 115, sealing device 116, and sealing structure 133 only need to withstand pressures of up to 10 atm before the ice seal takes over. The sizes of first gap 140 and second 141 are not critical, but may be minimized so that ice fills them before the seal is subjected to pressures above 10 atm. In one embodiment, first gap 140 and second gap 141 may be less than 2.0 mm in width. Chamber 110 includes a suspension device 117 which prevents biological material or bag placed within pressure chamber from coming into contact with the walls of chamber 110. Suspension device 117 may be a net, a platform, a spacer, or any other suitable device.

Figure 7A:
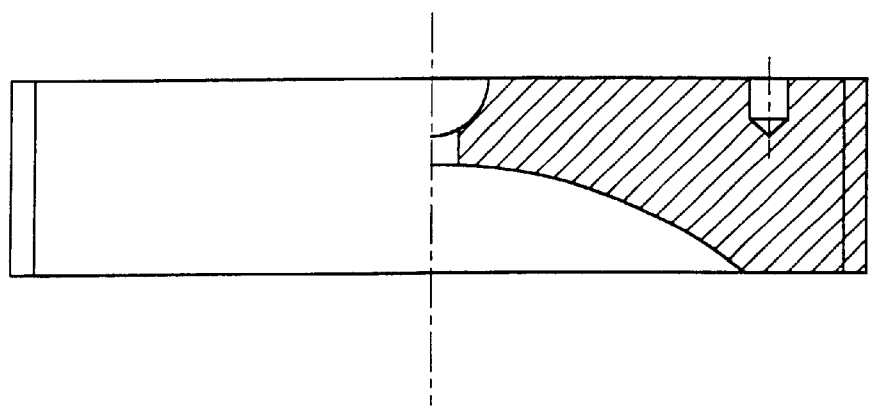
FIGS. 7A–7C show a cover retaining device of the preservation apparatus.
Figure 7B:
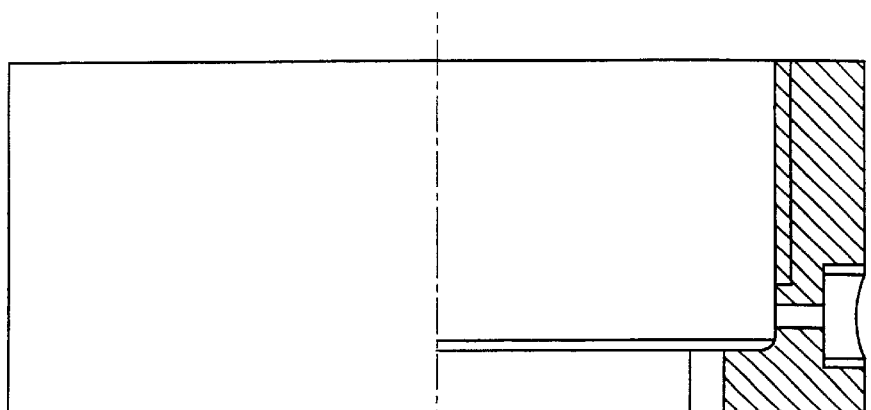
Figure 7C:
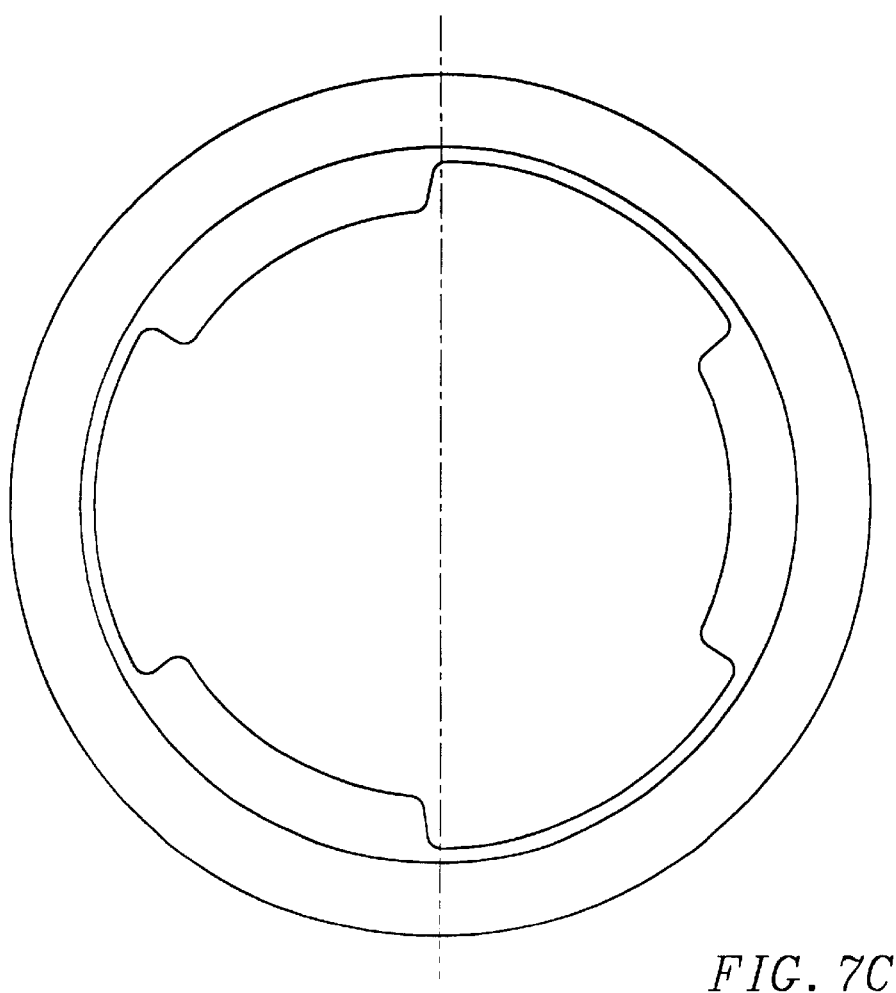

Cover 130 may be designed to be sealed to chamber 110 directly, or with the aid of a cover retaining device 135. Cover retaining device 135 may be designed to allow cover 130 to be installed and removed quickly and easily. Cover retaining device 135 may be coupled to chamber 110 via a bayonet-style connection, threads, or any other suitable coupling method. Cover retaining device 135 may include a centering pin 136 to keep cover retaining device 135 centered or attached to cover 130. Cover retaining device 135 may also include holes 137 to allow a wrench or other tool to be used with cover retaining device 135. Cover retaining device 135 may be produced in two separated pieces to simplify manufacturing. FIGS. 7A–7C show cutaway and top views of a two-piece cover retaining device 135.

Preservation apparatus 100 may include a pressure gauge 150 with an elastic membrane 151 placed within chamber 110. Pressure gauge 150 may include a relief valve 152 which prevents pressure within preservation apparatus 100 from exceeding a predetermined maximum.

EXAMPLE

The following is one example of the method of the present invention as used to preserve blood platelets. Heparin may be used as an anticoagulant before this process is begun.

1. Mix the platelets with a preservation solution of 2.9% gelatin, 0.44% sucrose, 1.17% glucose, and 0.49% NaCl.
2. Seal the platelets and preservation solution into a storage bag, making sure that any air has been pumped out The storage bag may be any standard platelet storage bag such as a flexible silicone rubber bag.
3. Cool the platelets and preservation solution to 15° C. within 1 hour.

Continuous agitation is required until the preservation solution becomes a gel.

4. Cool the storage bag to 6° C. to 8° C. within 1 to 1.5 hours.
5. Cool the preservation apparatus to 6° C. to 8° C.
6. Insert the storage bag into the preservation apparatus using the suspension device.
7. Fill the preservation apparatus with a pressure transfer fluid of 2.5% NaCl solution.
8. Seal the preservation apparatus, making sure it is completely full and no air is trapped inside.
9. Cool the preservation apparatus to −7.5±0.2° C. within 1.5 to 2 hours. The pressure transfer fluid is a fluid which expands when cooled or frozen, and thus will be able to exert a pressure upon the bag within the substantially fixed volume of the preservation apparatus. With the 2.5% NaCl solution, the water will begin to freeze at the walls of the pressure chamber. As the ice is formed at the walls of the pressure chamber, the expansion will create the high pressures required within the preservation apparatus, which will be transferred by the unfrozen fluid immediately surrounding the storage bag to the storage bag. The NaCl lowers the freezing point of the pressure transfer fluid, thus allowing the low temperatures required to be achieved before the entire volume of the pressure transfer fluid becomes frozen. The preservation solution has a lower freezing point than the pressure transfer fluid. The pressure inside the preservation apparatus will rise to 500 atm. As ice begins to form, pressure within the preservation apparatus will increase because ice and water are essentially non-compressible. The relationship between temperature and pressure here is consistent and predictable. The combination of the preservation solution, the high storage pressure, and the low storage temperature allows the platelets to be stored for up to 15 days. Erythrocytes may be stored up to 30 days and leukocytes up to 22 days using this method.

10. When the platelets are needed for use, allow the preservation apparatus to thaw completely at room temperature, approximately 20° C., before opening the preservation apparatus. Because the components in the preservation solution are all nontoxic, the platelets may be used immediately without further preparation.

The foregoing description of the invention has been presented for purposes of illustration and description. It is not intended to be exhaustive or to limit the invention to the precise forms disclosed. Many modifications and variations will be apparent. It is intended that the scope of the invention be defined by the following claims and their equivalents.

What is claimed is:

1. A method for preserving platelets for later direct transfusion into a patient, the method comprising:

forming a preservation medium by mixing plasma comprising platelets with gelatin where a concentration of gelatin relative to the plasma in the resulting preservation medium is between 1.0% to 3.0%, this gelatin concentration causing the preservation medium to (a) be sufficiently fluent at about 37° C. to allow platelets to move within the preservation medium, (b) transition from the fluent state to a gelatinous state below 15° C., and (c) be sufficiently gelatinous below 5° C. to substantially prevent platelets from moving freely within the preservation medium;

cooling the preservation medium to a temperature below 0° C.; and storing the preservation medium below 0° C. for at least 1 day at a pressure of at least 70 ATM.

2. The method of claim 1, wherein the preservation solution includes sucrose.

3. The method of claim 1, wherein the preservation solution includes less than 5% sucrose.

4. The method of claim 1, wherein the preservation solution includes 1.0% to 2.0% sucrose.

5. The method of claim 1, wherein the preservation solution includes glucose.

6. The method of claim 1, wherein the preservation solution includes less than 5% glucose.

7. The method of claim 1, wherein the preservation solution includes 1.0% to 3.0% glucose.

8. The method of claim 1, wherein the preservation solution includes sodium chloride.

9. The method of claim 1, wherein the preservation solution includes less than 5% sodium chloride.

10. The method of claim 1, wherein the preservation solution includes 0.2% to 0.6% sodium chloride.

11. The method of claim 1, wherein the preservation medium is stored at a pressure of 70 to 1000 ATM and a temperature of −12° C. to below 0° C. for the at least 1 day.

* * * * *